United States Patent [19]
Rhoads et al.

[11] Patent Number: 5,270,644
[45] Date of Patent: Dec. 14, 1993

[54] MAGNETOMETER FOR USE IN THE IN-SITU MEASUREMENT OF MAGNETOTACTIC BACTERIA IN AQUATIC ENVIRONMENTS AND METHOD OF USING SAME FOR PREDICTING AQUATIC HYPOXIA

[75] Inventors: Donald C. Rhoads; Sandor G. Mulsow, both of Falmouth, Mass.

[73] Assignee: Science Applications International Corporation, San Diego, Calif.

[21] Appl. No.: 787,303

[22] Filed: Oct. 29, 1991

[51] Int. Cl.$^5$ .................... G01N 27/74; G01R 33/12; G01R 33/00
[52] U.S. Cl. ................................. 324/204; 324/262
[58] Field of Search ................ 324/204, 244, 262, 261

[56] References Cited
PUBLICATIONS

Parsons et al. (1985), *A Manual of Chemical and Biological Methods for Seawater Analysis:* Pergamon Press, N.Y., N.Y. Chapter 7, pp. 135–144.
J. Kanwisher, "Polarographic Oxygen Electrode", Linmol Oceangr. 4, pp. 210–217 (1959).
R. Blakemore, "Magnetotactic Bacteria" *Science,* vol. 190, pp. 377–379 (Oct. 24, 1975).
Winterie, et al., "Mechanisms of Photochemical Reaction in Solution, Photochemical Oxidation of Tris (2,2'-bipyridyl) ruthenium (II) by Molecular Oxygen", *J. Am. Chem. Soc.,* vol. 98, No. 12, pp. 3719–3721, (Jun. 1976).
Revsbech, et al., "Oxygen in the Sea Bottom Measured with a Microelectrode", *Science,* vol. 207, No. 21, pp. 1355–1356 (Mar. 21, 1980).
R. P. Blakemore, "Magnetotactic Bacteria", *Ann. Rev. Microbiol.,* vol. 36, pp. 217–238 (1982).
Sporman, et al., "Chemotactic, Magnetotactic and Tactile Behaviour in a Magnetic Spirillum" *Microbhiol. Letters.,* vol. 22, pp. 171–177, (1984).
Blakemore, et al., "Microaerobic Conditions are Required for Magnetite Formation Within Aquaspirillum Magnetotacticum", *Geomicrobiol. J.,* vol. 4, No. 1, pp. 53–71, (1985).
A. M. Spormann, "Unusual Swimming Behaviour of a Magnetotactic Bacterium", *Microbiol. Ecol.,* vol. 45, pp. 37–45, (1987).
Tokar, et al., "The Use of Fiber Optic Sensors for In-situ Chemical Measurements in the Ocean", *Geotechnical Engineering of Ocean Waste Disposal, ASTM STP* 1087, pp. 65–75 (1990).

*Primary Examiner*—Walter E. Snow
*Attorney, Agent, or Firm*—Fitch, Even, Tabin & Flannery

[57] ABSTRACT

An apparatus and method for the in-situ measurement and prediction of the onset of hypoxic conditions in aquatic media is disclosed. The apparatus includes a magnet and sensor for concentrating and measuring biogenic magnetic fields produced by ambient populations of microaerophilic magnetotactic bacteria in aquatic sedimentary environments and means for correlating the measured data with oxygen content in the locations monitored.

16 Claims, 7 Drawing Sheets

▨ = SEDIMENT

▩ = MAGNETOTACTIC BACTERIA + SED.

MEASUREMENT SEQUENCE

MAGNETOMETER FOR USE IN THE IN-SITU MEASUREMENT OF MAGNETOTACTIC BACTERIA IN AQUATIC ENVIRONMENTS AND METHOD OF USING SAME FOR PREDICTING AQUATIC HYPOXIA

FIELD OF THE INVENTION

The present invention is generally related to methods and apparatus for the monitoring of dissolved oxygen in marine and other aquatic environments and more specifically to methods and apparatus for predicting the onset of high oxygen demand and water column hypoxia in bottom sediments through the measurement of ambient populations of magnetotactic bacteria.

BACKGROUND OF THE INVENTION

Marine and other aquatic sediments containing labile or reactive organic matter such as sewage, fish wastes, fish food and algal detritus in amounts over about 3% by weight total organic carbon (TOC) typically have a high sediment oxygen demand (SOD). This is due to the high rate of oxidation of such organic matter. In aquatic environments that receive high input rates of such reactive organic matter, SOD builds up over time until the oxygen demand is much greater then the supply of oxygen from the overlying water column. When oxygen demand exceeds supply, the overlying water column can be depleted of sufficient oxygen to support higher forms of aquatic life such as edible crustaceans and fish. It is, therefore, most important that the earliest stages of elevated SOD be predicted or detected to locate those areas of the sea floor that are potential candidates for developing hypoxic bottom water. Such prediction or detection will provide an opportunity to manage or otherwise control sources of organic enrichment before the environment becomes inhospitable to aquatic life.

Direct monitoring of dissolved oxygen (DO) in near-bottom marine sediment has been the traditional approach used to assess oxygen enrichment or depletion conditions in overlying water columns. Heretofore, it has been proposed to directly monitor DO using (1) chemical methods such as Winkler titration, (2) electro-optical methods such as fiber optic chemical sensors, and (3) polarographic electrodes.

Winkler titration requires that a small volume of water be recovered from a body of water. The sampling process must be carefully controlled so that the sample is not exposed to contamination by other sources of oxygen. The recovered sample is placed into glass bottles and the inventory of oxygen fixed with a reagent. The weight or volume of oxygen is measured by calorometric titration and expressed as the weight or volume of oxygen per unit volume of water. The Winkler titration method is limited to water column measurements and is not amenable to long time-series measurements as discrete water samples must be taken, usually by hand. The expense of taking time-series samples of water for titration analysis over extended periods of time makes this technique inappropriate for extended sampling in the field.

Fiber optical chemical sensors have been developed for monitoring dissolved oxygen in blood and appear to have potential for monitoring dissolved oxygen in aquatic systems. While such optical fibers may be insensitive to chemical poisoning they appear to be vulnerable to biofouling.

Polarographic membrane/electrode measurements of dissolved oxygen are among the more widely used means for measuring either the partial pressure of oxygen (volume or weight of oxygen per unit volume of water) or the flux of electrons (the oxidation-reduction "redox" potential $E_h$, expressed as millivolts). Such instruments may be lowered into the water or sediment columns for the purpose of making instantaneous measurements of DO concentration or $E_h$ values immediately around the probe. Alternatively, such polarographic devices may be incorporated into chambers placed on the sea bottom for the purpose of making time-series measurements of water trapped inside a respiration chamber. The chamber is closed on all sides except the bottom and is carefully placed onto the sediment surface. The open bottom is then gently forced a few centimeters into the sediment layer in order to prevent exchange of the water trapped inside the chamber with outside ambient water. Such a method is used to measure the uptake or release of oxygen into the supernatant water above the bottom in the chamber over time periods ranging from a few minutes to a few hours. The resulting time-series measurements are used to calculate SOD expressed either as weight or volume of oxygen consumed or released from the sediments per unit volume of water per unit time per unit area of bottom. Such polarographic electrode measurements of dissolved oxygen are limited to water column measurements. Also, the length of deployment is limited by fouling of the external membrane surface of the electrode by marine growth and the poisoning of the electrode by hydrogen sulfide in the water. Further, when polarographic electrodes are placed in respiration chambers, the measured values of oxygen consumption are sensitive to the rate of stirring of the water. These measurements are short term (a few hours) and not amenable for routine long-term monitoring as the chamber inhibits the supply of oxygen to the area of bottom being measured.

In use, it is found that all of the foregoing methods are subject to wide temporal and spatial variations. In many cases, by the time low oxygen partial pressures in the overlying water are detected and measured, mass mortalities of aquatic fauna have already taken place. Furthermore, with existing polarographic techniques, it is difficult to measure DO gradients within laminar sub-layers to detect the early onset of hypoxia. This is mainly because of the large bulk dimensions of currently available off-the-shelf polarographic DO probes. While smaller research polarographic probes have been developed to profile DO on a millimeter-by-millimeter scale, they are very fragile and not suited for rapid and efficient routine surveying of the sea floor.

Accordingly, there are continuing needs for improved apparatus and methods which simply and reliably allow (1) time-integrated measurement of the organic loading of a sea floor well in advance of the onset of bottom water hypoxia and (2) the making of numerous measurements over large areas in a survey day to locate and map zones of impending high surface SOD. The present invention satisfies such needs by use of in situ magnetometry to predict the onset of high SOD and water column hypoxia before biological resources are suffocated.

SUMMARY OF THE INVENTION

The present invention comprises an apparatus and method for predicting the onset of high oxygen demand in bottom sediments in fresh and salt water environments (SOD) through the measurement of ambient populations of magnetotactic bacteria.

It is known that certain types of aquatic bacteria such as *Aquaspirillum magnetotacticum* are magnetotactic, that is, they tend to swim along magnetic field lines following the vertical component of the earth's magnetic field. It is found that these bacteria are magnetically polarized in such a way that they swim almost exclusively vertically, that they tend to congregate mainly at the redox boundary in the bottom sediments and are substantially absent from the surface water layers when high concentrations of oxygen are present. It has also been found that (1) all magnetotactic bacteria, as a physiological group, only grow, and indeed, thrive in oxygen concentrations of between about 3 to about 5 percent saturation (microaerobic conditions) and (2) the relative position of the redox boundary and the bacteria within the sedimentary layer provide a measure of the SOD level, i.e. low when bacterial abundance is low, high when the bacterial abundance is high. Detection and measurement of a generalized upward movement of the microaerophilic magnetic bacteria will indicate the onset of a high SOD well in advance of detection by conventional oxygen measuring techniques.

With the apparatus and method of this invention, a time-series of in-situ measurements of the vertical location of the redox boundary as manifested in biogenic magnetic intensity can be made both at the sediment/water level and within the sediment column itself. These data can then be correlated with the actual oxygen levels present within the associated pore waters.

In its most basic embodiment, the apparatus of the present invention is a magnetometer comprising both a magnetic means for concentrating magnetotactic bacteria in a sediment bed toward the magnetometer and magnetic field measuring means for locating the concentrated bacteria and measuring the intensity of the biogenic magnetic field resulting from such concentration.

As used in the method of the present invention, a steady magnetic field of between about 1 and 10 gauss is applied by the magnetic means, as a result of which, the magnetotactic bacteria are caused to swim through the sediment pore water toward either the north or south pole of the magnetic means (depending upon the hemisphere in which the apparatus is being used) where they are concentrated for subsequent measurement. Following the concentration of the magnetotactic bacteria near the measurement device, the sediment column is then scanned by the magnetic field intensity measuring means to locate the vertical position of the concentrated bacteria within the sediment bed and to measure the biogenic magnetic field intensity of these populations. Time-series measurements of both the position and cumulative intensity of the concentrated bacterial population is a time-integrated indirect measurement of redox boundary movement and a predictor of future SOD. When the position of the magnetotactic bacteria is below the surface of the sediment and the magnetic intensity is weak, SOD should also be low. When the magnetic signature moves toward the surface and increases in strength, SOD is increasing.

BRIEF DESCRIPTION OF THE DRAWINGS

The various features and advantages of the present invention may be more readily understood with reference to the following detailed description taken in conjunction with the accompanying drawings, wherein like reference numbers refer to like structural elements, and in which.

DETAILED DESCRIPTION OF THE INVENTION

The present invention comprises both an apparatus and a method for predicting the onset of high oxygen demand in aquatic media. This is accomplished through (1) the concentration and measurement of biogenic magnetic fields produced by ambient populations of microaerophilic magnetotactic bacteria in aquatic sedimentary environments and (2) the correlation of these data with oxygen content in the location monitored.

Magnetotactic bacteria are known to swim along magnetic field lines and are, accordingly, influenced by the earth's magnetic field. It has been reported that the magnetotaxis of these particular bacteria is due to the presence of small magnetite crystals which are precipitated intracellularly within the bacterial cell structure (about 20 to 1000 cystals per bacterium). Because of their small size (400 to 1200 angstroms) these magnetic particles behave as single domain magnets. Thus, the earth's magnetic field acts on the bacterial dipole in the same way as it interacts with a compass needle. Because of this, magnetotactic bacteria largely swim in unison along magnetic field lines following the vertical component of the earth's magnetic field. The bacteria swim along the lines of magnetic inclination toward the south magnetic pole in the southern hemisphere and swim toward the north magnetic pole in the northern hemisphere, increasing in inclination angle with increasing latitude. Because of such inclination, north-seeking bacteria predominantly found in the northern hemisphere swim toward the North magnetic pole downward or upward along the lines of local magnetic inclination. Similarly, south-seeking bacteria predominantly found in the southern hemisphere are also directed toward the south magnetic pole. Consequently, magnetotactic bacterial cells in either hemisphere are magnetically polarized relative to the earth's polarity and swim almost exclusively upward and downward along the local lines of magnetic inclination. As they move into the sediment, it is found that these microaerophillic bacteria seek a level in the bottom where microaerobic conditions exist. Under these conditions, such bacteria are located underneath the intensively bioturbated sedimentary zone near to or at the redox boundary where $E_h$ (redox potential)=0, and are substantially absent from surface waters or sediments with positive or negative $E_h$ values.

Commonly, between about 1000 and about 10,000 bacteria/ml of sediment slurry occur in both fresh and salt water environments. Such bacteria have also been found in high densities in the basins of water purification plants, sewage-treatment oxidation ponds and in natural sediments with a high organic content. Most importantly, the bacteria within the sediment continually adjust their positions to remain within the 3 to about 5 percent D.O. saturation horizon. Magnetic crystals will not precipitate within the bacterial cells in higher or lower partial pressures of dissolved oxygen. Further, in such sediments, it is found that the directional movement of the microaerophilic bacteria can be easily manipulated by exposing them to a secondary magnetic field which is greater than that of the earth's magnetic field. The observations that magnetotactic bacteria are microaerophilic, can be manipulated by a secondary magnetic field, and seek out the redox boundary in sediments all combine to form the basis for the method and apparatus of the present invention.

Figure 1A:
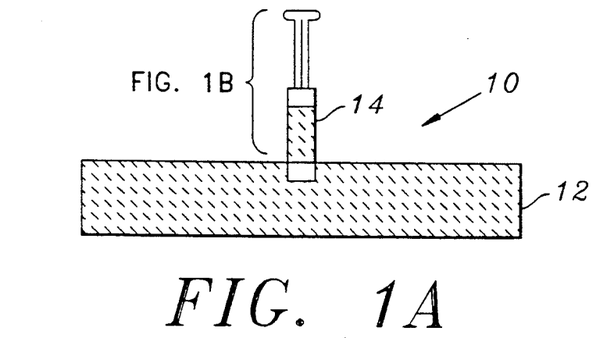
FIG. 1A is a schematic representation of a first embodiment of the apparatus of the present invention.

A simplified first embodiment of the apparatus 10 of the present invention is illustrated in FIG. 1A. As shown, the apparatus comprises a syringe 14 for coring a sediment sample in a tray of laboratory mud 12. By operation of the syringe 14, a sample of sediment is withdrawn from the mud tray 12 into the syringe for processing by the apparatus 10.

Figure 1B:
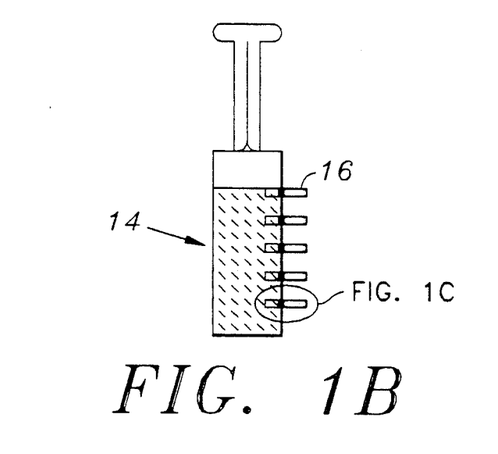
FIG. 1B is an enlargement of a sampling column included in the apparatus of FIG. 1A.

As shown in greater detail in FIG. 1B, the syringe comprises a plastic core with axially spaced side openings for a plurality of magnetic traps 16. The traps 16 function to trap and concentrate magnetotactic bacteria and include means (not shown) for measuring the vertical location and the biogenic magnetic field intensity of the trapped bacteria.

Figure 1C:
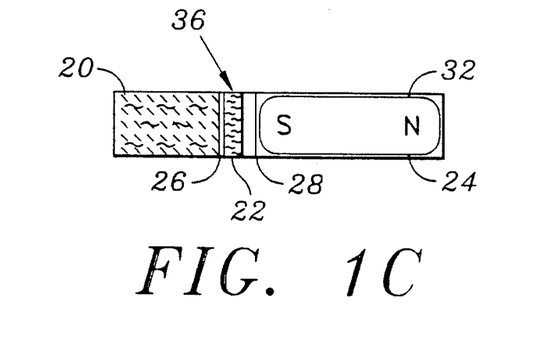
FIG. 1C is an enlargement of a magnetic trap included in the column of FIG. 1B.

As shown in still further detail in FIG. 1C, each trap 16 is comprised of three chambers identified as sediment chamber 20, trap chamber 22 and magnet chamber 24, respectively. Separating the three chambers are filters 26 and 28. Filter 26 may be formed of sterilized cotton or Millipore ® filter membrane and is mounted between chambers 20 and 22 to allow the passage of magnetotactic bacteria but not sediment particles. Filter 28 may be formed of a Millipore ® 0.2 micrometer membrane and is mounted between chambers 22 and 24 to prevent the further passage of the magnetotactic bacteria. Located within chamber 22 is a magnetic intensity measuring sensor 30, such as a sensitive Hall generator manufactured by F.W. Bell, Inc. of Orlando, Fla. Within chamber 24 is a conventional bar magnet 32. Typically each of the traps 16 is about 1 cm in diameter and about 7 cm in total length.

Figure 2:
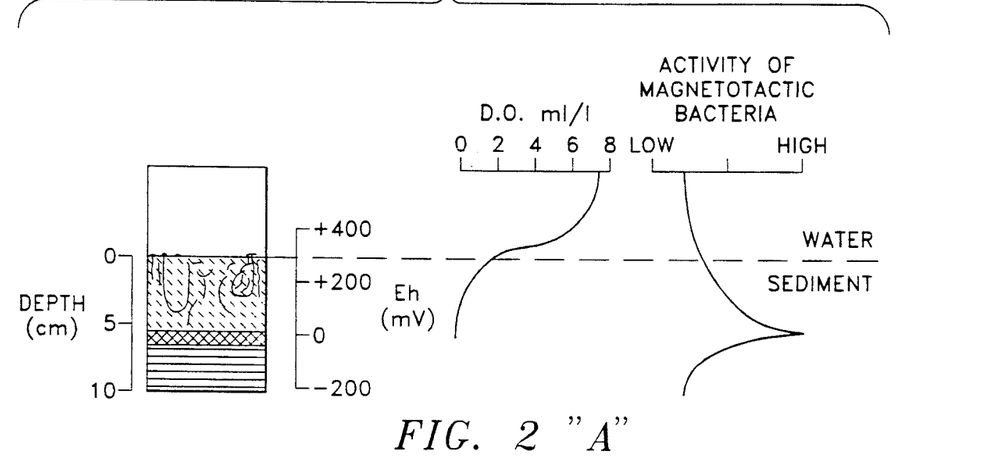
FIGS. 2A and 2B comprise graphs giving the relationship between magnetic measurements and oxygen levels as determined by the method of the present invention.

In use, sediment chamber 20 receives a portion of the sediment column through its open near end. Under the influence of bar magnet 32, any magnetotactic bacteria therein the sediment migrate through filter 26 into trap chamber 22 where they accumulate. After a period of time, the magnetic activity at each of the trap chambers 22 is measured by its associated sensor 30. The intensity readings from the sensors 30 may be correlated with the pore water oxygen levels at the depths at which the samples were taken to generate an oxygen level and $E_h$ profile for the sediment core as shown in FIG. 2 where the location of magnetotactic bacteria relative to the bioturbated zone and redox boundary in a sedimentary bed are depicted in a schematic diagram. As shown at "A," the redox boundary and underlying anoxic layer are about 5 cm below the surface of the sediment bed in this hypothetical example. Also, the level of dissolved oxygen (DO) may vary from 0.1–0.5 mg/l at the redox boundary to about 7.5 mg/l or more at the surface of the well oxygenated overlying water column. These conditions represent a bottom having a low potential for developing hypoxic bottom water. Note that the maximum concentration of magnetotactic bacterial activity is at the redox boundary whereas the surface has a low level of magnetotactic bacterial activity. As shown at "B," the depiction is of the location of the redox boundary under conditions of high SOD. Note that the redox boundary is now at the surface of the sediment bed as is coincident with the level of maximum magnetotactic bacterial level. Also, the level of dissolved oxygen (DO) varies from 0 mg/l at the redox boundary to about 0.1 to 0.5 mg/l within the viscuous laminar layer of water in contact with the surface of the sediment column. These are typical conditions that precede bottom water hypoxia.

Figure 3A:
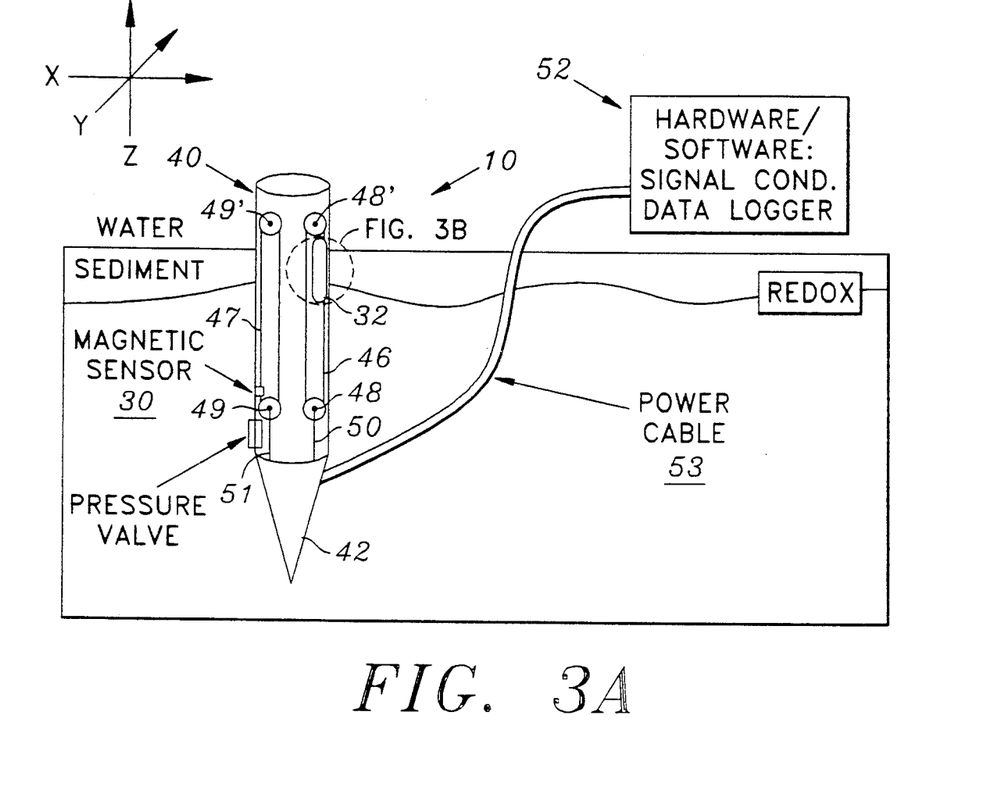
FIG. 3A is a schematic representation of a second embodiment of the apparatus of the present invention.
Figure 3B:
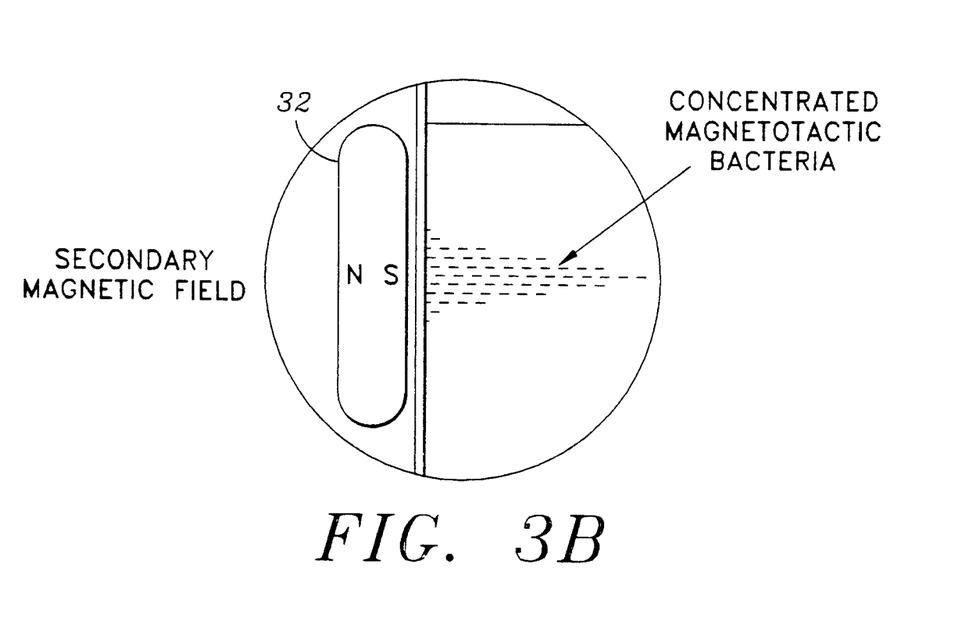
FIG. 3B is an enlargement of portion of the sensor shown in FIG. 3A.

FIGS. 3A and B are a schematic depiction of a second, and more advanced embodiment of the apparatus 10 of the present invention. As shown therein, the apparatus 10 comprises a hollow water-tight, non-magnetic, preferably polymeric sensor tube 40 having a pointed bottom 42 to facilitate penetration of the bottom sediment. In use, the tube 40 is typically placed in the sediment layer by divers to a depth well below the redox boundary and is anchored by means of wall friction with the surrounding sediment.

Inside of sensor tube 40 is (are) movable magnet(s) 32. The magnet 32 is placed against an interior wall of sensor tube 40 and may be either a permanent magnet or an electromagnet. The magnetic field generated by the magnet 32 extends vertically from above the sediment-water interface downward into the sediment column for several centimeters (Z axis). Such positioning concentrates ambient magnetotactic bacteria in the sedimentary layer into a narrow band by drawing them horizontally to the external surface of the sensor tube 40 (See FIG. 3B). In the northern hemisphere, the bacteria seek the magnetic north pole and in the southern hemisphere, they seek the magnetic south pole. FIG. 3A is configured for a northern hemisphere condition. The magnet(s) used must be several centimeters in length (Z axis), as the average location of the population of magnetotactic bacteria within the sediment bed can change over time (See FIG. 2). Also, located inside of sensor tube 40 is a magnetic intensity sensor means 30. There are a number of measuring devices which can be used in the present embodiment for this purpose. One such device comprises a Hall Generator, such as the Model GH600 made by the F. W. Bell Co.. As an active magnetic field intensity sensor, such a Hall Generator is capable of measuring a magnetic field strength threshold of about 0.02 Gauss.

The sensor 30 and the magnet 32 are positioned on individually movable, nonmagnetic, vertically disposed conveyor belts 46 and 47, respectively. The belt 46 is supported at opposite ends by non magnetic guide wheels 48, 48' having axles secured to the interior wall of the tube 40. In a like manner, the belt 47 is supported at opposite ends by non magnetic guide wheels 49, 49' having axles secured to the interior wall of the tube 40. The wheels 48 and 49 function as drive wheels for the conveyor belts 46 and 47 respectively and are coupled to the driving shafts 50 and 51 of internally programmable stepper motors (not shown) located within pointed end 42 and operated by control signals from a remote system controller 52 via a power cable 53. In addition to the conveyor belt stepper motors, the pointed end 42 houses a stepper motor for rotating the conveyor belts about the vertical axis (Z) of the sensor tube 40, the conveyors being mounted for such rotation by cross supports and vertical pivots (not shown).

Figure 4:
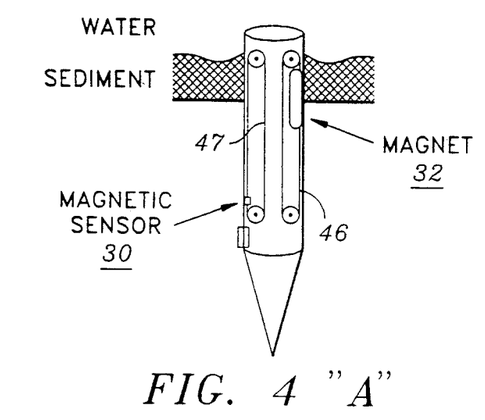
FIG. 4 shows at A, B, C, D and E the measurement sequence used in the method of the present invention as shown in FIG. 3A.

As represented in FIG. 4, at the start of the concentration phase of the measurement operation, ("A") the magnet 32 is situated at its uppermost position on its conveyor belt 46 while the magnetic field sensor 30 is at its lowermost position of its conveyor belt 47. The magnet 32 is maintained at the starting position, usually for a period of several hours, to concentrate the magnetotactic bacteria at or near the outer surface of tube 40 (See FIG. 3B). Then, to scan the profile of the sediment and measure the intensity and location of the biogenic magnetic field produced by the foregoing concentration phase, system controller 52 sends control signals via the cable 53 which cause the stepper motors to drive the conveyor belts 46 and 47 as shown at "B" in FIG. 4, with the magnet 32 moving down and the sensor 30 moving up until the positions of the magnet and the sensor are reversed as shown at "C". Such opposing vertical movements of the sensor 30 and magnet 32 is necessary as the Hall Generator must be at least 20 centimeters away from the magnet when activated. If the Hall Generator is located closer than this, the background magnetic field produced by magnet(s) 32 creates too much magnetic noise to detect and measure the much weaker magnetic field generated by the magnetotactic bacteria. Once the vertical positions of magnet 32 and sensor 30 are exchanged, the entire conveyer-belt system is rotated in the X/Y Plane 180°, as shown at "D" and "E" in FIG. 4. Such rotation is accomplished by the additional stepper motor housed in the pointed end 42 and brings the sensor means 30 into position to scan the upper few centimeters of the position where the magnet was previously positioned.

Once the sediment profile has been scanned by the Hall Generator as described above, the operational sequence is reversed by the system controller 52 from "E" to "D" to "C" to "B" to "A" as shown in FIG. 4, but at a new "A" position changed slightly in the X-Y plane to avoid measurement in exactly the same place (profile). In new position "A" the bacteria are again concentrated near the outer wall of the sensor tube 40 as shown in FIG. 3B. After each such measurement cycle, the concentrating magnet(s) 32 must be redeployed because, in the absence of the "concentrating" magnetic field, the magnetotactic bacteria will soon randomly disperse back into the ambient sediment in response to earth's magnetic dipole. In this regard, it is typically found that after about 60 minutes, the biogenic intensity signal drops to levels too low to be effectively measured with the Hall Generator. Thus, once measurement of a first profile is completed, a different profile is measured starting from a new measurement position slightly offset horizontally from the previous one, with the concentration and measurement procedure as described above being repeated.

Such time-series measurements of both the position of the bacteria and the cumulative magnetic intensity of the bacterial populations is a time-integrated measure of the sediment redox boundary and a predictor of future sediment oxygen demand. As previously noted and shown in FIG. 2, when the location of the magnetotactic bacteria is low in the sediment column and the magnetic signal is weak, SOD should be low. When the magnetic signature moves toward the sediment surface and the signal intensity increases, SOD is also increasing.

Figure 5:
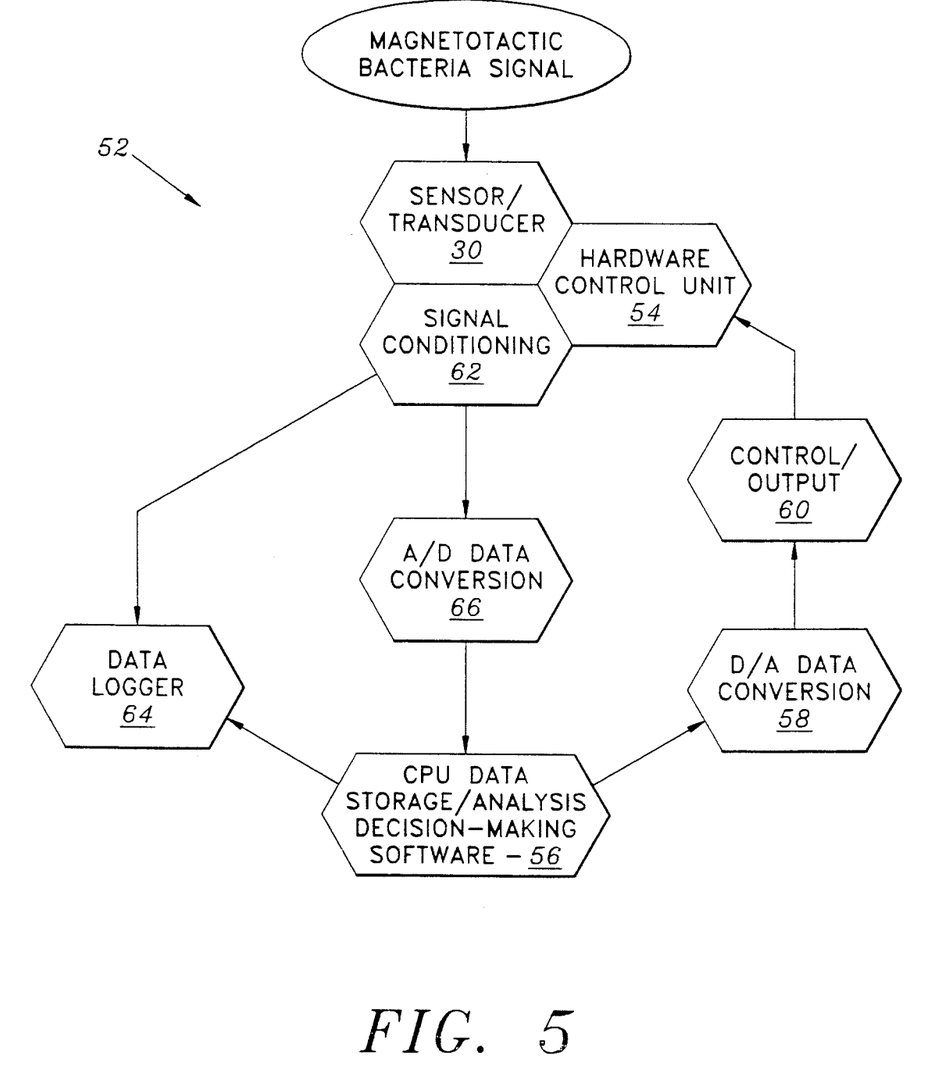
FIG. 5 is a schematic diagram of the control system configuration used for the in-situ measurement, recording, and correlation of the data transmission of magnetotactic bacteria in sediments.

For control of in-situ measurements as previously described, and the recording and transmission of data relating to the biogenic magnetic activity levels in the sediments monitored, apparatus 10 further comprises the system controller 52. The configuration of the several elements comprising the controller 52 and the several functions performed thereby are depicted in FIG. 5. As illustrated, the concentration and measurement of biogenic magnetic signals is a function of the positioning of magnet 32 and sensor 30, which is controlled by hardware control unit 54. Hardware control unit 54 may comprise an A/D board manufactured by Real Time Devices, Inc. and controls both the measurement frequency and sequence as directed through the decision making software in a programmable CPU 56. The CPU 56 may comprise an AT IBM compatible machine manufactured by DTK and typically is shore based and connected to controller 52 either by cable or by radio telemetry. The position control decisions from the CPU are transferred to the hardware control unit 54 and then to the stepper motors in the sensor tube 40 through a conventional D/A converter 58 and output controller 60 as illustrated. The magnetic intensity signal from sensor 30, after being conditioned in a conventional signal conditioner 62 to remove background ambient magnetic "noise," is passed to a conventional data logger 64. On command from CPU 56, either the data exiting from conditioner 62 and passing through A/D converter 66, or the accumulated data in logger 64 are transmitted to the CPU for storage and subsequent analysis.

Figure 6:
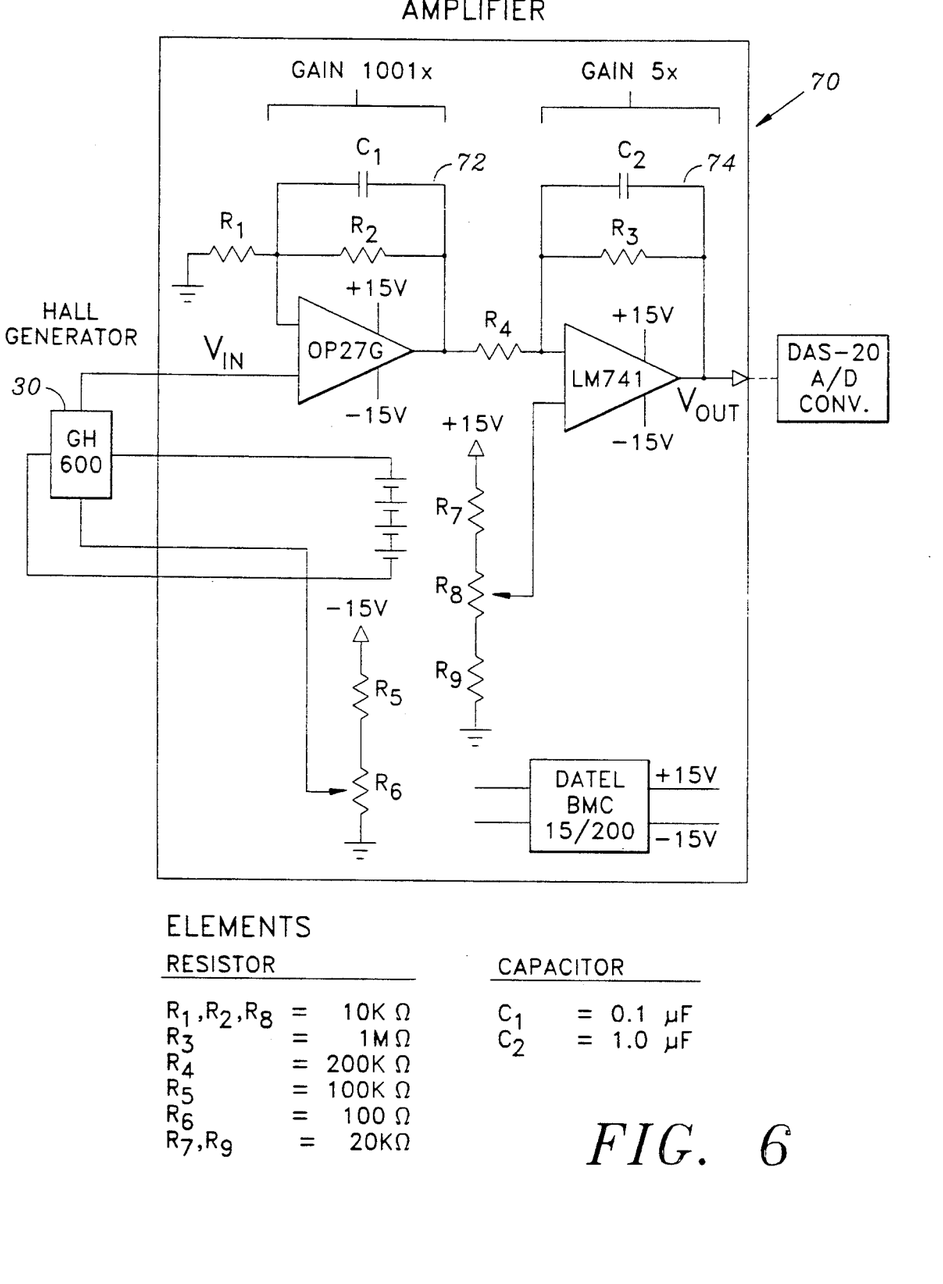
FIG. 6 illustrates a circuit diagram for a Hall Generator magnetic intensity sensor used in the apparatus of the present invention.
Figure 7A:
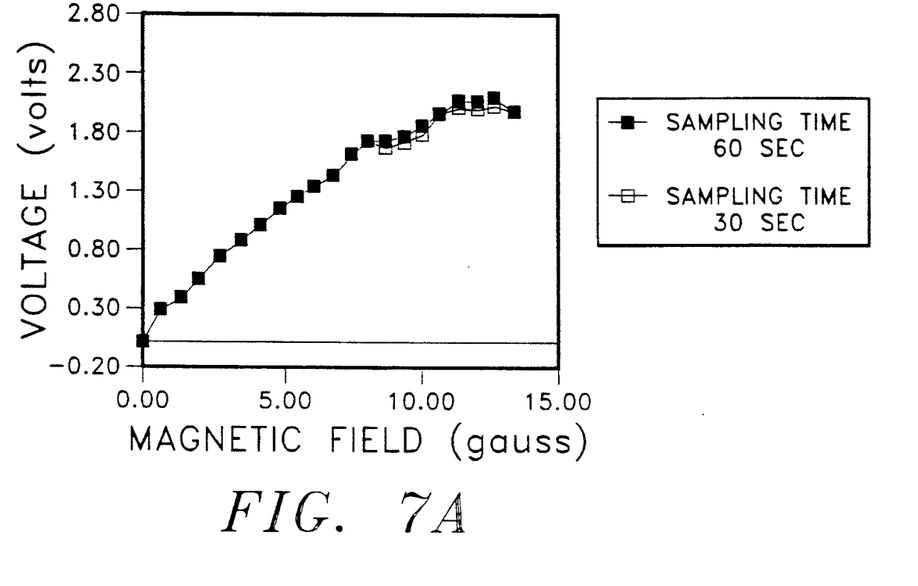
FIG. 7A is a calibration curve and FIG. 7B is a graph of the output for the sensor of FIG. 6.

Because of the relatively small size of the signal the Hall Generator used in sensor means 30, addition amplification and excitation means are required to obtain satisfactory signals for the use described above. One such amplifier system 70 is illustrated in FIG. 6 and comprises a custom designed system for driving the F.W. Bell Hall generator. More particularly, as shown, the system 70 comprises a pair of cascaded operational amplifiers 72 and 74 which achieve a total gain of about 5000. An actual calibration curve for the amplifier sensor system of FIG. 6 in volts as a function of the applied magnetic field in Gauss, is shown as FIG. 7A. For such calibration, sampling was at one Hz for 30 seconds and at one Hz for 60 seconds. The response of the Hall Generator is not significantly different in magnetic fields up to about 8 Gauss.

Figure 7B:
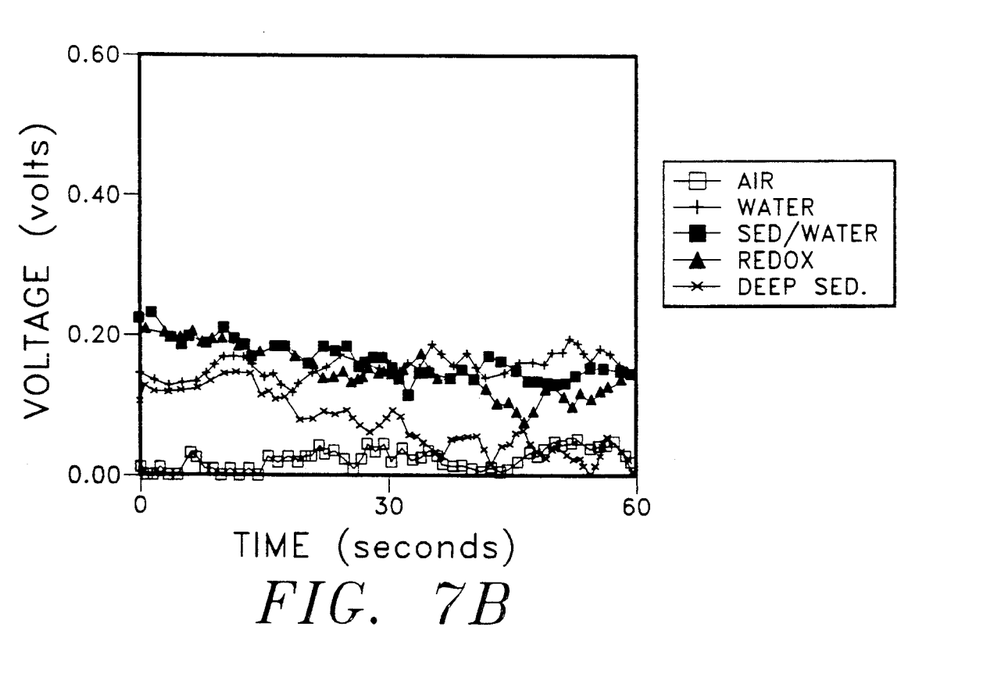

FIG. 7B is an example of the FIG. 6 Hall Generator output from scanning a natural sediment column containing magnetotactic bacterial populations from the organically enriched intertidal zone of Boston Harbor, Boston, Mass. The sampling rate was one Hz and the output was recorded (ASCII file), analyzed and plotted with QPRO 2.0 software. Note from the data displayed in FIG. 7B that: (1) the output signal stabilized after about 30 seconds, (2) the air calibration variance was related to random fluctuations in the earth's magnetic field, ambient magnetic noise and the excitation voltage for the Hall Generator, (3) the "deep" sediment anoxic signal is comparable to the air calibration signal, (4) the elevated voltage signal corresponding to the magnetic bacterial signals for the sediment-water interface and the redox boundary indicate that the magnetotactic bacteria are near to the surface of the bottom sediments, and (5) the magnetic signal in the overlying water is also high as the bacteria have moved out of the bottom sediments and are actually growing on the sensor tube (40) indicating that the sediment-water interface has a low dissolved oxygen content, i.e., is hypoxic, as shown in FIG. 2 and independently confirmed by $E_h$ measurements.

ADVANTAGES OF THE INVENTION

The present invention offers a number of advantages as compared to the prior art methods previously described. For example, unlike Winkler titration methods the apparatus of the present invention can make its measurements remotely in the sediment layer without having to acquire a subset of water samples for wet chemical analysis. Unlike the direct monitoring method, the cylindrical design of the sensor tube 40 offers little or no impedance to the flow of water around it or the accumulation and concentration of the magnetotactic bacteria therein so that can be left in place for extended periods of time. Further, because both the magnet 32 and sensor 30 are located inside water-tight sensor tube 40 and, therefore isolated from the medium being monitored, biogenic magnetometry is immune to bio- and chemical fouling as the measurement device is isolated from the external magnetic medium that it measures. The coupling between the sensor and the external environment is an electromagnetic field which is immune to biological and chemical fouling.

Thus there has been described a new and improved method and apparatus for the in-situ estimation of oxygen levels in aquatic media and the prediction of hypoxic conditions therein. It is to be understood that the above described embodiments are merely illustrative of some of the many specific embodiments which represent applications of the principles of the present invention. Clearly, numerous other arrangements can be readily devised by those skilled in the art without departing from the scope of the present invention, as defined in the present claims.

We claim:

1. A magnetometer apparatus for use in predicting aquatic hypoxia comprising:
    containment means for positioning in an aquatic sediment bed;
    magnet means disposed within said containment means for attracting and concentrating magnetotactic bacteria in the sediment bed;
    magnetic field intensity sensor means disposed within said containment means for sensing a biogenic magnetic field resulting from such concentration; and
    control and computational means for acquiring from the sensor means and correlating signals relating the biogenic magnetic field.

2. The magnetometer of claim 1 wherein:
    the containment means comprises a nonmagnetic hollow water-tight tube capable of being inserted into and anchored within the sediment bed and a conveyor system mounted within the tube and comprising a pair of internally mounted nonmagnetic vertical conveyor means onto one of which the magnet means is mounted, and onto the other of which the magnetic field intensity sensor means is mounted; and
    the apparatus further comprises:
        first programmable means adapted to receive control signals from said control means for causing the conveyer means to move the magnet and sensor means vertically within the hollow tube; and
        second programmable means adapted to receive control signals from the control means for causing a rotation of the conveyer system in an X/Y plane so that at the completion of its vertical movement, and rotation, the sensor means is located at the position formerly occupied by the magnet means.

3. The apparatus of claim 2 wherein the conveyer means are mounted on opposite sides of a vertical axes of the hollow tube and simultaneously move the magnet and sensor means in opposite vertical directions.

4. The apparatus of claim 1 wherein the magnet means comprises a bar magnet or magnets.

5. The apparatus of claim 1 wherein the magnet means comprises an electromagnet.

6. The apparatus of claim 1 wherein the magnet means produces a magnetic field between about 1 and about 10 gauss.

7. The apparatus of claim 1 wherein the sensor means comprises a Hall Generator.

8. A method for predicting hypoxic conditions in an aquatic media, comprising:
    (a) concentrating a population of magnetotactic bacteria in aquatic sediment to generate a biogenic magnetic field;
    (b) determining the vertical position of the population within aquatic sediment;
    (c) measuring the intensity of the biogenic magnetic field at the vertical position; and
    (d) correlating the measured intensity of the biogenic magnetic field to the level of oxygen at the vertical position.

9. The method of claim 8 wherein step (a) comprises lowering a container housing magnet means into the aquatic sediment.

10. The method of claim 9 wherein step (c) comprises sensing the biogenic magnetic field with sensor means spaced from the magnet means.

11. The method of claim 10 further comprising moving the magnet means in opposite vertical directions between measurements of the biogenic magnetic field intensity.

12. The method of claim 10 further comprising repeating steps (a), (b) and (c) at different positions within the aquatic sediment.

13. A magnetic method for predicting aquatic hypoxic conditions by correlating measured intensity of biogenic magnetic fields produced by ambient populations of magnetotatic bacteria in aquatic sedimentary environments, comprising the steps of:
    (a) placing in an aquatic sediment bed a water-tight, nonmagnetic sensor tube containing a movable magnet, a movable magnetic intensity sensor and drive means for moving the movable magnet and sensor;

(b) concentrating the magnetotactic bacteria in the sediment bed at or near an outer surface of the sensor tube;

(c) at the conclusion of a preselected concentration time, actuating the magnetic field intensity sensor to measure the intensity of a biogenic magnetic field resulting from such concentration; and (d) transferring magnetic field intensity data from the sensor to a remote location for analysis.

14. The method of claim 13 further comprising the step of:

(e) actuating the drive means to cause the simultaneous and vertically opposite movement of the magnet and sensor to new vertical positions.

15. The method of claim 14 further comprising the step of:

(f) controlling the drive means from the remote location.

16. The method of claim 14 further comprising repeating steps (a) through (d) with the magnet initially placed at a slightly different position in the aquatic sediment until the aquatic sediment is scanned and an oxygen demand profile generated for the sediment.

* * * * *